United States Patent
Poezevara

(10) Patent No.: US 8,043,225 B2
(45) Date of Patent: Oct. 25, 2011

(54) ACTIVE IMPLANTABLE MEDICAL DEVICE EQUIPPED WITH MEANS FOR THE DIAGNOSIS OF RESPIRATORY DISORDERS, WITH SOPHISTICATED DETECTION OF RESPIRATORY CYCLES WITH ARTIFACTS

(75) Inventor: Yann Poezevara, Courcouronnes (FR)

(73) Assignee: ELA Medical S.A.S., Montrouge (FR)

( * ) Notice: Subject to any disclaimer, the term of this patent is extended or adjusted under 35 U.S.C. 154(b) by 1434 days.

(21) Appl. No.: 11/096,277

(22) Filed: Mar. 31, 2005

(65) Prior Publication Data

US 2005/0267380 A1    Dec. 1, 2005

(30) Foreign Application Priority Data

Apr. 5, 2004  (FR) ..................... 04 03528

(51) Int. Cl.
*A61B 5/08*    (2006.01)
(52) U.S. Cl. ....................... 600/536; 600/534
(58) Field of Classification Search ........... 600/529–537
See application file for complete search history.

(56) References Cited

U.S. PATENT DOCUMENTS

| | | | |
|---|---|---|---|
| 4,567,892 A | | 2/1986 | Plicchi et al. ............. 128/419 |
| 4,608,995 A | * | 9/1986 | Linnarsson et al. ......... 600/526 |
| 5,817,135 A | * | 10/1998 | Cooper et al. ............. 607/17 |
| 6,574,507 B1 | | 6/2003 | Bonnet ..................... 607/20 |
| 7,094,207 B1 | * | 8/2006 | Koh ........................ 600/529 |
| 2002/0169384 A1 | * | 11/2002 | Kowallik et al. ........... 600/529 |
| 2002/0183644 A1 | * | 12/2002 | Levendowski et al. ....... 600/544 |
| 2002/0193697 A1 | | 12/2002 | Cho et al. ................. 600/529 |
| 2005/0080460 A1 | * | 4/2005 | Wang et al. ............... 607/17 |
| 2005/0197674 A1 | * | 9/2005 | McCabe et al. ............ 607/9 |

FOREIGN PATENT DOCUMENTS

EP  0 702 977 A2  9/1995
WO  02/087433 A1  7/2002

* cited by examiner

*Primary Examiner* — Patricia Mallari
*Assistant Examiner* — Christian Jang
(74) *Attorney, Agent, or Firm* — Orrick Herrington & Sutcliffe, LLP

(57) ABSTRACT

An active implantable medical device comprising circuits for measuring trans-thoracic impedance and delivering an impedance signal varying with respiratory activity of a patient. A signal representative of the respiratory activity of the patient is delivered starting from the impedance signal, and circuits for diagnosing respiratory disorder analyze variations of the respiratory signal on a plurality of successive cycles to detect there a profile of predetermined variation in relation to a given respiratory disorder. The device also includes circuits for automatically controlling respiratory cycles with artifacts, able to identify in the impedance signal a jump of static impedance, and/or to identify in a respiratory cycle or in a sequence of respiratory cycles a predetermined singularity representative of a cycle with artifact.

21 Claims, No Drawings

ACTIVE IMPLANTABLE MEDICAL DEVICE EQUIPPED WITH MEANS FOR THE DIAGNOSIS OF RESPIRATORY DISORDERS, WITH SOPHISTICATED DETECTION OF RESPIRATORY CYCLES WITH ARTIFACTS

FIELD OF THE INVENTION

The present invention relates to the diagnosis of respiratory sleep disorders, such as apnea or hypopnea with an "active implantable medical device" as defined by the Jun. 20, 1990 directive 90/385/CEE of the Council of the European Communities, and more particularly to a device such as a cardiac pacemaker, defibrillator, or multisite device.

BACKGROUND OF THE INVENTION

Various techniques for detecting respiratory sleep disorders are known. These techniques implement a variety of sensors. For example EP-A-0 970 713 and its counterpart, U.S. Pat. No. 6,574,507, commonly assigned herewith to ELA Médical, describe diagnosis of the occurrence of an apnea starting from the minute-ventilation signal (the "VE signal," sometimes referred to as the "MV signal"), which is a parameter with physiological preponderance generally obtained by measuring a trans-thoracic impedance, giving a continuous indication of the respiration rate of the patient.

The detection of the apnea or of hypopnea makes it possible to diagnose conditions such as the syndrome of sleep apnea (SSA), obstructive apnea, or central apnea, which is a pathology likely to involve a number of disorders, such as diurnal hyper somnolence, heart rate disturbances, or hypertension. SSA can be defined by a significant recurrence of apnea or hypopnea associated clinical signs. An "apnea" or "respiratory pause" is a temporary pause of the respiratory function lasting longer than 10 seconds and occurring while the patient is sleeping. An "hypopnea" is defined as a significant decrease of the minute-ventilation, for example, a decrease of more than 50%, compared to an average of former reference, but without pause of the respiratory function (the minute-ventilation is the product of the amplitude multiplied by the frequency of the successive respiratory cycles).

The measurement of the minute-ventilation necessary for this detection of the apnea or of hypopnea is carried out by injecting of impulses of a constant current of a few hundred microamperes at a frequency of some Hertz between two electrodes laid out in the rib cage of the patient, or between the case of the implanted device and an electrode, for example, a stimulation electrode. The variations of impedance reproduce the variations of thoracic volume, with peaks of impedance at the time of an inspiration, i.e., when the lungs are filled with air, and a decreasing impedance over time as the air is expired from the lungs.

It was noted in clinical studies that a system implementing a respiratory activity sensor recording variations of pulmonary volume at the thoracic level can be deluded in certain circumstances, leading to risks of false positive and false negative readings that can disturb interpretation of the signals by the device and thus lead to an erroneous diagnosis. Some of these disturbances can be eliminated by known adapted filtering techniques.

The trans-thoracic impedance varies according to the resistivity of tissue at the time current impulses are injected. As this resistivity depends primarily on the quantity of air in the lungs and the quantity of blood in the cardiac cavities, the impedance signal collected is modulated at the same time by breathing and the heart rate of the patient. The impedance is also modulated by variations in spacing between the measurement electrode and the case of the implanted device, which can change as the heart beats. These cardiac components can be eliminated by simple low-pass filtering, the heart rate being in the majority of the cases about three times higher than the respiratory frequency. In addition, in order to extract from the signal only the respiratory component (only the dynamic variation is significant), it is advisable to eliminate any static impedance related to the impedance from tissue recorded in a stable body position and in the absence of any breathing and cardiac beat. This static component can be eliminated by implementation of a high-pass filter.

When the trans-thoracic impedance is used to estimate the minute-ventilation and to control the heart rate, this estimate of the minute-ventilation is based on an average of several successive respiratory cycles, so that the impact of some respiratory cycles with artifacts remains low.

The starting point of the present invention lies in the observation that certain phenomena, which are not eliminated by existing low-pass and high-pass filtering, are able to disturb measurement of the trans-thoracic impedance. In particular, if one wishes to use the trans-thoracic impedance to follow instantaneous variations in respiratory activity, in particular to detect apnea and hypopnea, it is essential to eliminate all the cycles with artifacts, at the risk of producing false positives and false negatives, that can lead to erroneous diagnoses of respiratory disorders of the patient. Thus, the trans-thoracic impedance can be modified by a movement of the patient, or varied by contractions of the diaphragm during an obstructive apnea. These phenomena can produce artifacts that will disturb the system and can lead to erroneous detection of particularly full or fast respiratory cycles, or of low amplitude or long periods, which can lead to a false positive.

Another type of artifact can result from the presence in the impedance signal of a component related to cardiac beats that is not eliminated by existing high-pass filters. Indeed, in certain circumstances (for example, if bradycardia and hyperventilation occur at the same time), the respiratory frequency and the heart rate can become sufficiently close that the cardiac beats influence the impedance signal to a significant degree. The heart rate can then be incorrectly interpreted as the respiration rate, which may mask the presence of an hypopnea or an apnea (a false negative, at the time a true respiratory pathological event occurs).

When external equipment is being used (e.g., polysomnography), these disturbances can be detected by the person interpreting the signals, who can decide not to take into account one or more channels when the signal appears disturbed. This subjective appreciation of the signals is not possible in an implanted apparatus, however, which functions in an entirely automatic way according to rules defined by an analysis algorithm.

OBJECTS AND SUMMARY OF THE INVENTION

A goal of the present invention is to improve analysis of respiratory activity by an implanted device, and in particular to eliminate false positives and false negatives resulting from cycles with artifacts not taken into account by known filtering means.

The detection of cycles with artifacts according to the invention applies advantageously to implanted devices including means for diagnosing and treating respiratory disorders, which require a cycle by cycle follow-up of the respiratory activity of the patient, so as to be able to diagnose without delay occurrence of a pathological respiratory event.

To this end, the invention proposes a medical device that includes in a way in itself known (for example, according to the above-mentioned EP-A-0 970 713 and its counterpart, U.S. Pat. No. 6,574,507, commonly assigned herewith to ELA Médical): means for measuring the trans-thoracic impedance, delivering an impedance signal that varies with respiratory activity of the patient; means for processing the impedance signal able to deliver, starting from this signal, a respiratory signal presenting a succession of consecutive respiratory cycles and representative of respiratory activity of the patient; and means for diagnosis of respiratory disorder, able to analyze variations of the respiratory signal over a plurality of successive cycles.

The device of the present invention also includes means for automatic control of respiratory cycles with artifacts, comprising means able to identify, in the impedance signal, a jump of static impedance, or means able to identify, in a respiratory cycle or a sequence of respiratory cycles, a predetermined singularity representative of a cycle with artifact.

The means able to identify a jump of static impedance can include means able to detect saturation of an amplifying circuit of the impedance signal processing means circuit, or the crossing of a threshold value in a circuit of digitalization of the impedance signal processing means circuit, or a modification of the cut-off frequency of the aforesaid means of high-pass or low-pass filtering.

The means able to identify a predetermined singularity can in particular include means able to detect a respiratory cycle in which:
  the period is shorter than a first limit, for example, 2 seconds, or
  the period is shorter than a second limit, for example, 10 seconds, and presenting an increase higher than a third limit, for example, 4 seconds, compared to the period of the preceding cycle, or
  the amplitude presents an increase higher than a fourth limit compared to the amplitude in the preceding cycle, and for which the means for the diagnosis did not detect a respiratory disorder in the preceding cycle. This fourth limit can be a predetermined value, for example, 50 millivolts, or a relative value, determined compared to an average of the amplitudes measured over one former period, for example, +25% compared to the average of the amplitudes measured during a previous day.

According to various forms of implementation of the invention, in the event of identification of a static jump of impedance or a predetermined singularity:
  the means for the automatic control of respiratory cycle artifacts inhibit the means for diagnosing respiratory disorder, preferably for a minimal length of time of temporization given after identification of the static jump of impedance or the predetermined singularity;
  when the means for the diagnosis calculates and updates an average of the respiratory cycle periods, the means for the automatic control of respiratory cycle artifacts inhibit the update of the aforementioned average;
  the means for the automatic control of respiratory cycle artifacts invalidate the aforementioned profile of predetermined variation eventually detected by the means of diagnosis, in the event of identification of jumps of static impedance or in the event of predetermined singularities of which the number exceeds a fifth limit given during a sequence of former cycles, for example, four identifications for a sequence of sixteen former cycles.

DETAILED DESCRIPTION OF THE INVENTION

A more detailed example of implementing the present invention will now be described.

The invention can in particular be applied to the active implantable medical devices marketed by ELA Médical, Montrouge, France. These devises are microcompressor-based devices comprising circuits for receiving, formatting, and treating electric signals collected by implanted electrodes. It is possible to charge therein by telemetry the software that will be stored and will be carried out to implement the below-described functions of the invention.

The invention is applicable to an implanted device comprising means for detecting the occurrence of apnea or hypopnea by analyzing the respiration rate of the patient during his or her sleep, this rate being given by the evolution over the course of the time of the minute-ventilation signal (MV signal).

The MV signal is a parameter with physiological preponderance obtained by a trans-thoracic measurement of impedance. This measurement is operated between two electrodes laid out in the rib cage of a patient, or between an electrode (for example, a stimulation electrode, if the implanted device is a cardiac pacemaker) and the case of the device. The impedance is measured by injecting a constant current of a few hundred microamperes, at a frequency of some Hertz, typically 8 Hz. This technique, for example, is described by Bonnet J L et al., Measurement of Minute-Ventilation with Different DDDR Pacemaker Electrode Configurations, *PACE*, vol. 21, 98, Part 1, and is implemented in devices like ELA Médical's *Chorus RM* 7034.

The device considers that there is apnea when it detects a respiratory pause lasting longer than 10 seconds, a phenomenon that is easy to detect by follow-up of the MV signal. To detect hypopnea, the device can compare successive sliding of the MV signal, established, for example, over a 10 second duration. If between two consecutive averages a significant decrease of the minute-ventilation is detected, for example, a decrease of more than 50%, then the device considers that there has been an hypopnea.

As indicated above, the invention proposes implementing a monitoring of the respiratory signal so as to identify certain categories of artifacts and to engage in preventive actions during the diagnosis.

The first series of artifacts taken into account by the invention are those related to movement, which are probably most frequent and generally lead to a sudden modification of the static impedance. To this end, the device of the present invention comprises in the circuit for measuring the trans-thoracic impedance means for identifying a static impedance jump. For that, the software of the device can be programmed to function to scan in real time one or more parameters of the measuring circuit in order to detect, in particular:
  the saturation of an amplifier,
  extreme values reached in the digitalization circuit, or
  modification of a cut-off frequency in the filtering of the signal.

If a static jump of impedance is detected, the device reacts by suspending the diagnosis of a respiratory sleep disorder as long as the signal is not stabilized to its new value, i.e., during the time necessary for filtering of the new static component. It is possible to introduce a temporization before reactivating the function of diagnosis.

According to another aspect of the invention, the artifacts can also be identified based on their effects on detection of respiratory cycles, starting from the amplitude or the period of these cycles, or the variation of these parameters cycle to cycle. Indeed, it has been noted in practice that the respiratory period is generally rather stable, and thus presents rather slow variations. Therefore, when an apnea occurs, a significant variation of the respiratory period appears, but this period passes directly from a normal value (typically 3 to 4 seconds) to a high value (longer than 10 seconds, in accordance with the definition of apnea). Therefore, variations of periods of about several seconds, but shorter than 10 seconds, can lead to suspicion of an artifact. One can also define the minimum duration of a respiratory cycle (for example, 2 seconds), such that any cycle of shorter duration can lead to suspicion of an artifact.

It is also possible to analyze the amplitude of the respiratory cycles. The measuring equipment of the minute-ventilation is dimensioned to be able to measure large respiratory cycles, occurring during an effort, for example. But when a large cycle occurs in a perfectly isolated way, it is still possible to suspect an artifact. To take these situations into account, the algorithm according to the invention analyzes the successive respiratory cycles after having determined and classified them (e.g., amplitude, period). Any respiratory cycle fulfilling one of the following criteria then will be regarded as an artifact:

- the period of the cycle is less than or equal to X seconds (for example, shorter than X=2 seconds),
- the period of the cycle is less than 10 seconds and presents an increase in Y seconds (for example, Y=4 seconds) compared to the period of the preceding cycle,
- the amplitude of the cycle increased by Z units compared to the preceding cycle, if this preceding cycle does not coincide with a diagnosis of apnea or of hypopnea (because in this last case a significant ventilatory resumption is awaited).

Parameter Z can take a predetermined value (for example, Z=50 mV) or a relative value, calculated on a representative number of respiratory cycles (for example, an increase in Z=25% compared to the average in the amplitudes measured during the previous day).

In the presence of cycles considered as artifacts, the device can react in various ways. First of all, cycles considered as artifacts can be simply kept out in the management of the various functions of the device (typically, the enslavement function) and will not be taken into account for the update of the average of the respiratory cycles representative of the running rate, which average will be used to detect hypopnea.

Another action concerns inhibiting the means for diagnosing respiratory disorders in the event of cycles with artifacts, so as to suspend the search for an apnea or an hypopnea, in the same manner as on detection of a jump of static impedance. This inhibition of the diagnosis can be started either on identification of an isolated cycle with artifact, or only in the event of too frequent repetition of the cycles with artifacts. For example, the algorithm determines with each cycle the number of cycles with artifacts that have occurred during the last 16 respiratory cycles (sliding window). If this account reaches a determined threshold, then the algorithm invalidates the apnea or hypopnea possibly diagnosed during these preceding cycles.

In the alternative, if the system has several sensors for detection of respiratory disorders (for example, a sensor for oxygen saturation in addition to the circuit measuring the trans-thoracic impedance), the algorithm can inhibit only the research of the apnea or hypopnea based on the sensor of the trans-thoracic impedance, by continuing the research of the respiratory disorders starting only from the signal of oxygen saturation.

One skilled in the art will appreciate that the present invention can be practiced by other than the described embodiments which are presented for purposes of illustration and not of limitation.

I claim:

1. An active implantable medical device comprising:
   means for measuring a trans-thoracic impedance, the means for measuring the trans-thoracic impedance delivering an impedance signal varying with respiratory activity of a patient, the impedance signal comprising a cardiac beat, a breathing beat, and a static component, the static component comprising tissue impedance varying with a body position of the patient in the absence of the breathing beat and the cardiac beat;
   means for processing the impedance signal, the means for processing the impedance signal eliminating the cardiac beat from the impedance signal and delivering a respiratory signal over consecutive respiratory cycles, the respiratory signal comprising the breathing beat and the static component;
   means for diagnosing a respiratory disorder by analyzing variations of the respiratory signal over the consecutive respiratory cycles; and
   means for automatically controlling the consecutive respiratory cycles comprising:
      means for identifying artifacts in the respiratory signal including a jump of the static component of the impedance signal, caused by a change of the body position of the patient, or
      means for identifying, in at least one respiratory cycle of the consecutive respiratory cycles, a predetermined singularity representative of a respiratory cycle with an artifact including the jump of the static component of the impedance signal.

2. The device of claim 1, wherein the means for processing the impedance signal further comprises an amplifying circuit, wherein the means for identifying artifacts in the respiratory signal detects saturation of said amplifying circuit.

3. The device of claim 1, wherein the means for identifying artifacts in the respiratory signal detects a crossing of a threshold value in a digitalization circuit of the means for processing the impedance signal.

4. The device of claim 1, wherein the means for identifying artifacts in the respiratory signal detects a modification of a cut-off frequency of a high-pass filter or a low-pass filter.

5. The device of claim 1, wherein the means for identifying a predetermined singularity detects a respiratory cycle whose period is shorter than a first limit.

6. The device of claim 5, wherein the first limit is 2 seconds.

7. The device of claim 1, wherein the means for automatically controlling the consecutive respiratory cycles inhibits the means for diagnosing a respiratory disorder in the event of identification of a jump of the static component or the predetermined singularity.

8. The device of claim 1, wherein the means for automatically controlling the consecutive respiratory cycles inhibits the means for diagnosing a respiratory disorder for one minimal length of time of temporization given after identification of a jump of the static component or the predetermined singularity.

9. The device of claim 1, wherein the means for diagnosing a respiratory disorder calculates and updates an average of the periods of the consecutive respiratory cycles, and in which the means for automatically controlling the consecutive respiratory cycles inhibits the update of the average in the event of identification of a jump of the static component or the predetermined singularity.

10. The device of claim 1, wherein the means for automatically controlling the consecutive respiratory cycles invalidates detection of the respiratory disorder by the means for diagnosing in the event of identification of jumps of the static component or the predetermined singularities of which the number exceeds a fifth limit given during a sequence of former cycles.

11. The device of claim 10, wherein the fifth limit is four cycles during a sequence of sixteen former cycles.

12. An active implantable medical device comprising:
means for measuring a trans-thoracic impedance, the means for measuring the trans-thoracic impedance delivering an impedance signal varying with respiratory activity of a patient;
means for processing the impedance signal, the means for processing the impedance signal delivering a respiratory signal over consecutive respiratory cycles representative of the respiratory activity of the patient;
means for diagnosing a respiratory disorder by analyzing variations of the respiratory signal over the consecutive respiratory cycles; and
means for automatically controlling the consecutive respiratory cycles with artifacts comprising:
means for identifying a jump of static impedance, or
means for identifying, in at least one respiratory cycle of the consecutive respiratory cycles, a predetermined singularity representative of a respiratory cycle with an artifact,
wherein the means for identifying a predetermined singularity detects a respiratory cycle whose period is shorter than a second limit and an increase of the period of the respiratory cycle higher than a third limit compared to the period in the preceding respiratory cycle.

13. The device of claim 12, wherein the second limit is 10 seconds and the third limit is 4 seconds.

14. The device of claim 12, wherein the means for identifying a predetermined singularity detects a respiratory cycle whose amplitude presents an increase higher than a fourth limit compared to the amplitude in the preceding cycle, and for which the means for the diagnosis did not detect a respiratory disorder in the preceding cycle.

15. The device of claim 12, wherein the means for automatically controlling the consecutive respiratory cycles invalidates detection of the respiratory disorder by the means for diagnosing in the event of identification of jumps of static impedance or predetermined singularities of which the number exceeds a fifth limit given during a sequence of former cycles.

16. The device of claim 12, wherein the fifth limit is four cycles during a sequence of sixteen former cycles.

17. An active implantable medical device comprising:
means for measuring a trans-thoracic impedance, the means for measuring the trans-thoracic impedance delivering an impedance signal varying with respiratory activity of a patient, the impedance signal comprising a cardiac beat, a breathing beat, and a static component;
means for processing the impedance signal, the means for processing the impedance signal eliminating the cardiac component from the impedance signal and delivering a respiratory signal over consecutive respiratory cycles representative of the respiratory activity of the patient;
means for diagnosing a respiratory disorder by analyzing variations of the respiratory signal over the consecutive respiratory cycles; and
means for automatically controlling the consecutive respiratory cycles with artifacts comprising:
means for identifying a jump of the static component of the impedance signal, the static component measuring tissue impedance in a stable body position and in the absence of the breathing beat and the cardiac beat,
wherein the means for identifying ,a predetermined singularity detects a respiratory cycle whose amplitude presents an increase higher than a fourth limit compared to the amplitude in the preceding cycle, and for which the means for the diagnosis did not detect a respiratory disorder in the preceding cycle.

18. The device of claim 17, wherein the fourth limit is a predetermined value.

19. The device of claim 18, wherein the fourth limit is 50 millivolts.

20. The device of claim 17, wherein the fourth limit is a relative value, determined by comparison with an average of amplitudes measured over a former period.

21. The device of claim 20, wherein the fourth limit is +25% compared to the average of amplitudes measured over the previous day.

* * * * *